(12) United States Patent
Park et al.

(10) Patent No.: US 9,945,879 B2
(45) Date of Patent: Apr. 17, 2018

(54) CELL SMEARING APPARATUS AND CELL SMEARING METHOD

(71) Applicant: TCM Korea, Inc., Gyeonggi-do (KR)

(72) Inventors: Young Chul Park, Seoul (KR); Hee Jae Joo, Gyeonggi-do (KR); Dong Jin Shin, Gyeonggi-do (KR)

(73) Assignee: TCM KOREA, INC., Gyeonggi-do (KR)

( * ) Notice: Subject to any disclaimer, the term of this patent is extended or adjusted under 35 U.S.C. 154(b) by 0 days.

(21) Appl. No.: 14/392,285

(22) PCT Filed: Apr. 22, 2015

(86) PCT No.: PCT/KR2015/004020
§ 371 (c)(1),
(2) Date: Dec. 23, 2015

(87) PCT Pub. No.: WO2015/163688
PCT Pub. Date: Oct. 29, 2015

(65) Prior Publication Data
US 2016/0274135 A1    Sep. 22, 2016

(30) Foreign Application Priority Data
Apr. 23, 2014  (KR) .................. 10-2014-0048890

(51) Int. Cl.
*G01N 1/38*      (2006.01)
*G01N 35/00*     (2006.01)
*G01N 1/31*      (2006.01)
*G01N 35/10*     (2006.01)
(Continued)

(52) U.S. Cl.
CPC ..... *G01N 35/00029* (2013.01); *G01N 1/2813* (2013.01); *G01N 1/312* (2013.01); *G01N 35/00584* (2013.01); *G01N 35/10* (2013.01); *G01N 35/1016* (2013.01); *G01N 1/38* (2013.01);
(Continued)

(58) Field of Classification Search
USPC ............................................ 422/50, 500, 100
See application file for complete search history.

(56) References Cited

U.S. PATENT DOCUMENTS

| 5,282,978 A | 2/1994 | Polk, Jr. et al. |
| 5,441,699 A | 8/1995 | So et al. |
| 2010/0038244 A1* | 2/2010 | Wood .................. B01F 3/04531 204/468 |

FOREIGN PATENT DOCUMENTS

| EP | 0 448 837 A2 | 10/1991 |
| KR | 10-2002-0041172 A | 6/2002 |
| KR | 10-2005-0094604 A | 9/2005 |

(Continued)

*Primary Examiner* — Jyoti Nagpaul
(74) *Attorney, Agent, or Firm* — Christensen, Fonder, Dardi & Herbert PLLC (57) ABSTRACT

A cell smearing apparatus comprising: a mixed solution container accommodation unit accommodating a mixed solution container containing a mixed solution of cells and a preservation solution; a suction unit suctioning the mixed solution from the mixed solution container accommodated in the mixed solution container accommodation unit; a sensor unit sensing variation of the mixed solution suctioned by the suction unit; and a controller controlling a suctioning speed of the suction unit based on a value sensed by the sensor unit. The present invention allows cells to be examined to be smeared as a monolayer on a slide for microscopic examination.

4 Claims, 8 Drawing Sheets

(51) Int. Cl.
*G01N 1/28* (2006.01)
*G01N 1/40* (2006.01)
(52) U.S. Cl.
CPC ............ *G01N 2001/4088* (2013.01); *G01N 2035/00138* (2013.01)

(56) References Cited

FOREIGN PATENT DOCUMENTS

| KR | 10-2006-0103769 A | 10/2006 |
| KR | 10-1037239 B | 5/2011 |
| KR | 10-1317311 B | 10/2013 |
| KR | 10-2013-0125495 A | 11/2013 |

\* cited by examiner

CELL SMEARING APPARATUS AND CELL SMEARING METHOD

PRIORITY CLAIM

The present application is a National Phase entry of PCT Application No. PCT/KR2015/004020, filed Apr. 22, 2015, which claims priority from Korean Application No. 10-2014-0048890, filed Apr. 23, 2014, the disclosures of which are hereby incorporated by reference herein in their entirety.

FIELD OF THE INVENTION

The present invention relates to a cell smearing apparatus and a cell smearing method.

BACKGROUND

Histopathologic examination refers to the morphological examination with a microscope of tissue obtained through surgery or physiological examination or an organ obtained through pathological anatomy, and is particularly used in diagnosis of benignancy or malignancy of a tumor, a primary lesion and a metastasis lesion, the presence of effects of a carcinostatic agent or radiotherapy, the presence of an inflammatory lesion, the degree of cell metamorphosis, malformation, and the like.

Such histopathologic examination is performed through a series of processes of collecting detached cells, attaching a target cell to be examined to a glass slide through fine needle aspiration or smearing, fixing and dyeing to prevent deformation, and microscopic examination by a pathologist.

That is, for histopathologic examination, it is necessary to perform an operation of smearing cells to be examined onto a glass slide. However, conventionally, since such operation is manually carried out by an operator, there are problems such as a long operation time, exposure to foreign matter and contaminants during operation, and non-uniform smearing of cells onto the glass slide. Particularly, when cells are non-uniformly smeared onto the glass slide, only cells on the uppermost layer among the cells overlapping each other can be observed through microscopic examination, thereby making it difficult to find a malignant cell which can be present at a lower side of the cells overlapping each other.

SUMMARY OF THE INVENTION

It is an object of the present invention to provide a cell smearing apparatus which can automatically smear cells to be examined in a monolayer onto a slide.

It is another object of the present invention to provide a cell smearing method using the cell smearing apparatus.

In accordance with one aspect of the present invention, a cell smearing apparatus includes: a mixed solution container accommodation unit accommodating a mixed solution container containing a mixed solution of cells and a preservation solution; a suction unit suctioning the mixed solution from the mixed solution container accommodated in the mixed solution container accommodation unit; a sensor unit sensing variation of the mixed solution suctioned by the suction unit; and a controller controlling a suctioning speed of the suction unit based on a value sensed by the sensor unit.

The sensor unit may include a pressure sensor for sensing a pressure of suctioning the mixed solution, and the controller may control the suction unit to suction the mixed solution at a reduced speed when a pressure of suctioning the mixed solution sensed by the pressure sensor reaches a predetermined pressure.

The mixed solution container may include: an upper body accommodating the mixed solution; a lower body provided with a filter unit filtering the cells in the mixed solution and detachably coupled to the upper body; and a sealing member for securing air-tightness between the upper body and the lower body coupled to each other.

The filter unit may include a filter having a film shape and filtering the cells in the mixed solution; and a buffer portion provided to one side of the filter and compressing and buffering the filter with respect to the slide when the filtered cells are stamped on the slide, and the filter and the buffer portion may have a rectangular shape.

The suction unit may be provided to a tray, and the cell smearing apparatus may further include a transfer member transferring the tray in an up-down direction, and the transfer member may control a transferred distance of the tray through a stepper motor or an encoder motor.

The tray may include a drain accommodation unit accommodating a drain for discharge outside instead of passing through the filter when the upper body is separated from the lower body.

The tray may be connected to a valve, and the valve may include: a first inlet communicating with the suction unit; a second inlet communicating with the drain accommodation unit; an outlet through which a fluid having flowed through the first inlet and the second inlet is discharged; and a shut-off unit selectively opening or closing the first inlet and the second inlet.

The cell smearing apparatus may further include: a concentration analyzer measuring a concentration of the mixed solution in the mixed solution container accommodated in the mixed solution container accommodation unit; and a preservation solution supplier additionally supplying the preservation solution to the mixed solution container accommodation unit when the concentration of the mixed solution measured by the concentration analyzer is higher than a predetermined value.

The suction unit may be connected to a pump for suctioning the mixed solution, and the pump may be a peristaltic tube pump.

In accordance with another aspect of the present invention, a cell smearing method includes. (a) coupling an upper body of a mixed solution container to a mixed solution container accommodation unit of a case, the mixed solution container including the upper body and a lower body detachably coupled to the upper body; (b) lifting a tray to couple a suction unit of the tray to the mixed solution container accommodation unit; (c) suctioning the mixed solution of the mixed solution container accommodation unit through the suction unit; (d) lowering the tray to separate the lower body from the upper body; (e) coupling a slide to a slide accommodation portion of the case; and (f) lifting the tray to allow cells filtered through a filter of the lower body to be stamped on the slide coupled to the slide accommodation portion.

In the step of (c) suctioning the mixed solution of the mixed solution container accommodation unit through the suction unit, a pressure sensor may sense pressure of the mixed solution suctioned by a suction unit, and a controller may control the suction unit to suction the mixed solution at a reduced speed when the pressure of suctioning the mixed solution sensed by the pressure sensor reaches a predetermined pressure.

Before the step of (c) suctioning the mixed solution of the mixed solution container accommodation unit through the suction unit, (b') a concentration analyzer may measure a concentration of the mixed solution in the mixed solution container accommodated in the mixed solution container accommodation unit, and a preservation solution supplier may add the preservation solution to the mixed solution container accommodation unit when the concentration of the mixed solution measured by the concentration analyzer exceeds a predetermined value.

According to the present invention, it is possible to smear cells to be examined in a monolayer onto a slide for microscopic examination.

In addition, it is possible to prevent collected cells from being mixed with foreign matter or exposed to contaminants.

Further, it is possible to reduce consumption of time and labor for cell smearing.

DETAILED DESCRIPTION

Hereinafter, exemplary embodiments of the present invention will be described in detail with reference to the accompanying drawings. Throughout the specification and the accompanying drawings, like reference numerals denote like elements having the same or similar functions. Detailed descriptions of features or functions apparent to those skilled in the art will be omitted for clarity.

It will be understood that, although the terms "first", "second", "A", "B", "(a)", "(b)", etc. may be used herein to describe various elements, components, and/or regions in the following exemplary embodiments, these elements, components, and/or regions should not be limited by these terms. These terms are used only to distinguish one element, component, or region from another element, component, or region. It will be understood that when an element is referred to as being "connected", "coupled" or "joined" to another element, it can be directly connected, coupled or joined to the other element, or intervening elements may also be present. In contrast, when an element is referred to as being "directly connected", "directly coupled", or "directly joined" to another element, there are no intervening elements.

As used herein, the term "mixed solution" is defined as a mixed fluid of cells to be examined and a preservation solution for preserving the cells.

As used herein, the term "filtered solution" is defined as a fluid of the mixed solution from which the cells are filtered.

As used herein, the term "drain" is defined as a fluid of the filtered solution introduced into a tray through a drain inlet instead of a suction unit.

As used herein, the term "waste solution" generally refers to the filtered solution and the drain.

As used herein, the term "stamping" is defined as a series of processes of bring an object into contact with a target, compressing the object with respect to the target in a stamping manner, and releasing compressive force.

Next, a cell smearing apparatus according to one exemplary embodiment of the present invention will be described in detail with reference to the accompanying drawings.

Figure 1:
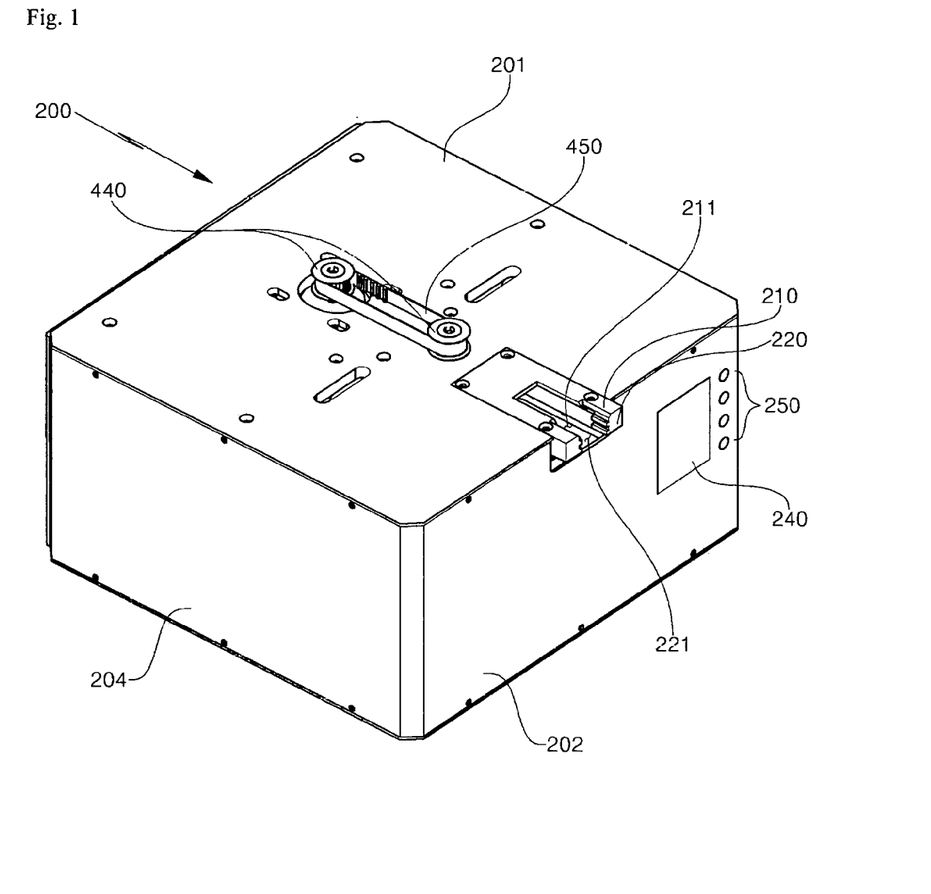
FIG. 1 is a perspective view of a cell smearing apparatus according to one exemplary embodiment of the present invention.
Figure 2:
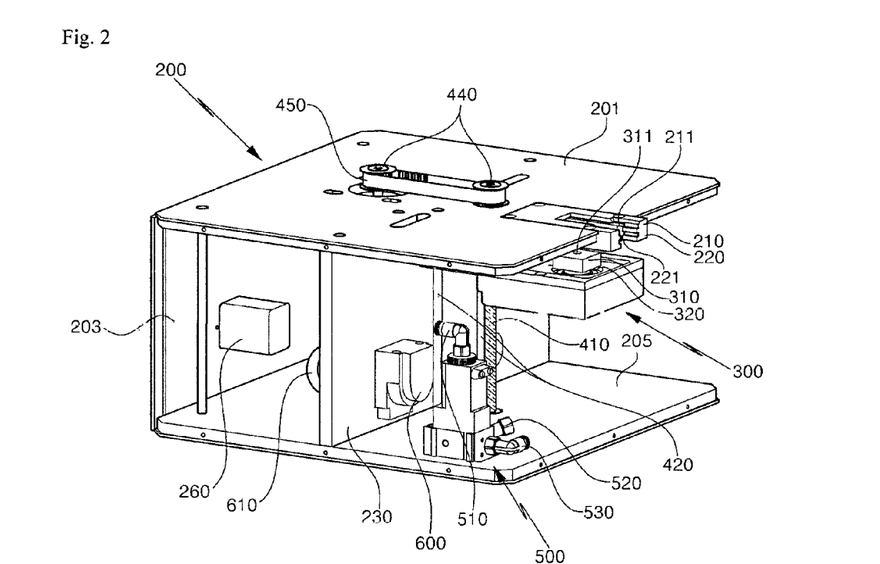
FIG. 2 is a perspective view of the cell smearing apparatus according to the exemplary embodiment of the present invention, from which a case is partially removed.
Figure 3:
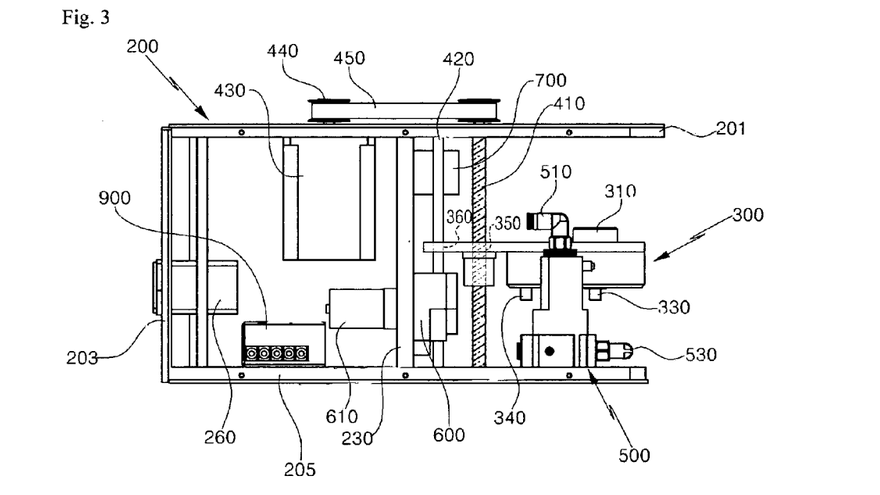
FIG. 3 is a side view of the cell smearing apparatus according to the exemplary embodiment of the present invention, from which the case is partially removed.
Figure 4:
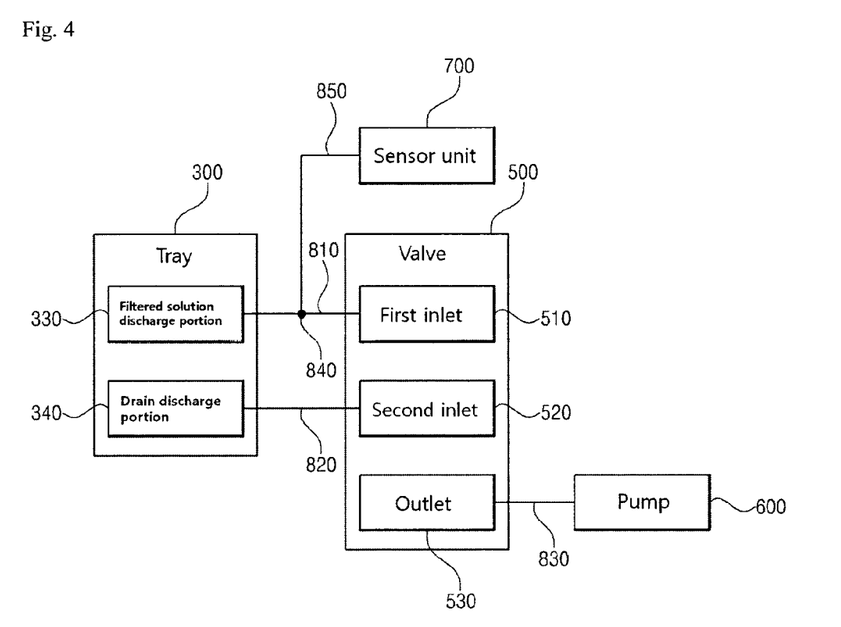
FIG. 4 is a block diagram of the cell smearing apparatus according to the exemplary embodiment of the present invention, illustrating a connection relationship between a tray, a valve, a pump and a sensor unit connected to each other via a tube.
Figure 5:
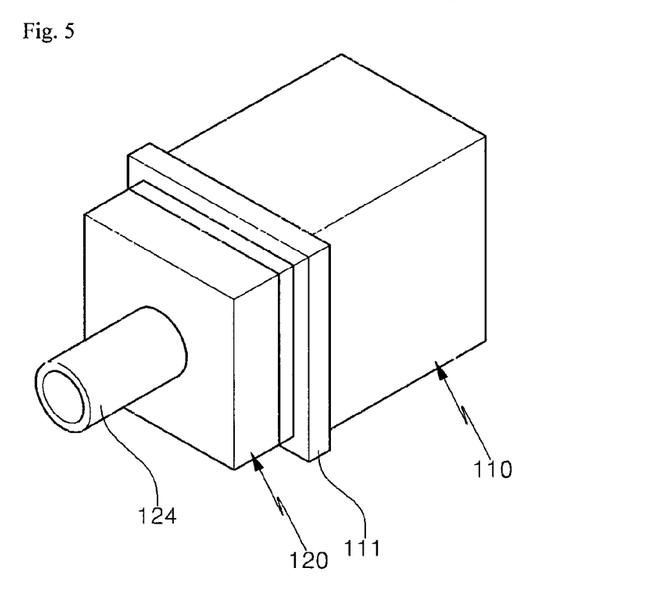
FIG. 5 is a perspective view of a mixed solution container of the cell smearing apparatus according to the exemplary embodiment of the present invention.
Figure 6:
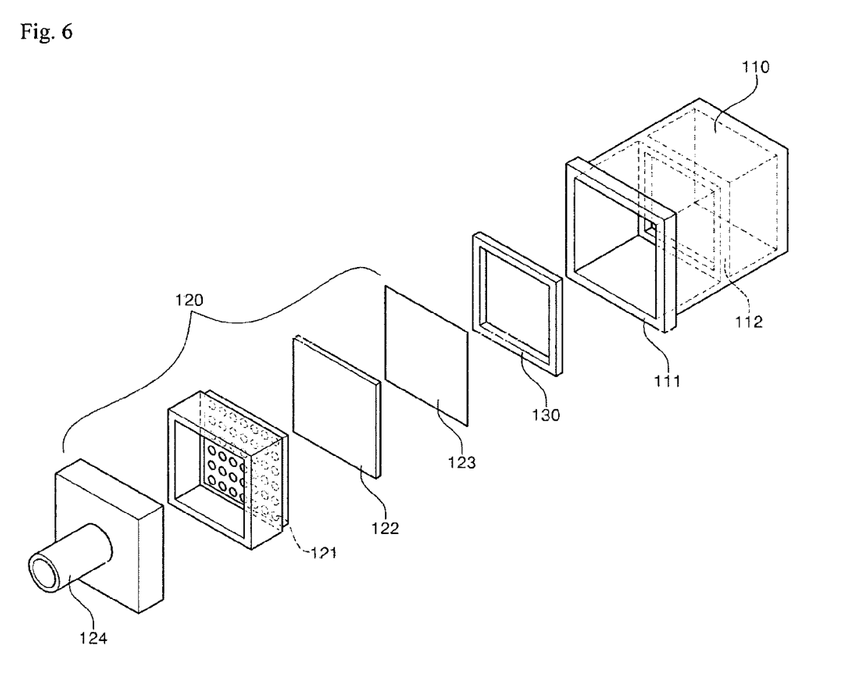
FIG. 6 is an exploded perspective view of the mixed solution container of the cell smearing apparatus according to the exemplary embodiment of the present invention.

FIG. 1 is a perspective view of a cell smearing apparatus according to one exemplary embodiment of the present invention; FIG. 2 is a perspective view of the cell smearing apparatus according to the exemplary embodiment of the present invention, from which a case is partially removed; FIG. 3 is a side view of the cell smearing apparatus according to the exemplary embodiment of the present invention, from which the case is partially removed; FIG. 4 is a block diagram of the cell smearing apparatus according to the exemplary embodiment of the present invention, illustrating a connection relationship between a tray, a valve, a pump and a sensor unit connected to each other via a tube; FIG. 5 is a perspective view of a mixed solution container of the cell smearing apparatus according to the exemplary embodiment of the present invention; and FIG. 6 is an exploded perspective view of the mixed solution container of the cell smearing apparatus according to the exemplary embodiment of the present invention. Here, it should be noted that the tube is omitted in FIG. 2 and FIG. 3 for convenience of description.

Referring to FIG. 1 to FIG. 6, a cell smearing apparatus according to one exemplary embodiment may include a mixed solution container 100, a case 200, a tray 300, a transfer member 400, a valve 500, a pump 600, a sensor unit 700, tubes 810, 820, 830, 850, a concentration analyzer (not shown), and a controller 900. It should be understood that the above features of the cell smearing apparatus are provided as one example of the cell smearing apparatus according to the present invention and are not essential features of the cell smearing apparatus according to the present invention.

The mixed solution container 100 is a container configured to accommodate a mixed solution of cells and a preservation solution.

In one exemplary embodiment, the mixed solution container 100 may include an upper body 110, a lower body 120, and a sealing member 130, as shown in FIG. 5 and FIG. 6.

The upper body 110 constitutes a sidewall of a space in which the mixed solution is accommodated. The upper body 110 is detachably coupled to the lower body 120 and has a shape corresponding to at least a portion of the lower body 120. In one exemplary embodiment, as shown in FIG. 5 and FIG. 6, the upper body 110 may have a hollow space of a rectangular shape (including a square shape) when viewed in a top plan view. It should be understood that the shape of the upper body 110 is not limited thereto.

In one exemplary embodiment, an outer wall of the upper body 110 may be provided with an outer protrusion 111, as shown in FIG. 5. The outer protrusion 111 may have a shape corresponding to a groove 211 formed on a mixed solution container accommodation unit 210 of the case 200 described below. With this structure, the upper body 110 can be secured to the case 200 by inserting the outer protrusion 111 of the upper body 110 into the groove 211 of the mixed solution container accommodation unit 210.

In one exemplary embodiment, an inner wall of the upper body 110 may be provided with an inner protrusion 112. The inner protrusion 112 serves to support the lower body 120 when the lower body 120 is inserted into the upper body 110. As described below, a sealing member 130 is disposed between the inner protrusion 112 and the lower body 120 to maintain air-tightness between the upper body 110 and the lower body 120.

The lower body 120 may be separably coupled to the upper body 110. In other words, the lower body 120 may be selectively coupled to the upper body 110. That is, the lower body 120 may be detachably coupled to the upper body 110.

In one exemplary embodiment, the lower body 120 may include a porous plate 121, a buffer portion 122, a filter 123, and an outlet 124, as shown in FIG. 6. Although a portion for the porous plate 121 and a portion for the outlet 124 may be provided as separate members in the lower body 120 as shown in FIG. 5, it should be understood that the lower body 120 may be provided as a one-piece structure. In one exemplary embodiment, as shown in FIG. 6, the lower body 120 may have a hollow space of a rectangular shape (including a square shape) when viewed in top plan view. With this structure, the lower body 120 may be inserted into the rectangular hollow space of the upper body 120. Obviously, the shapes of the upper and lower bodies 110, 120 are not limited thereto.

The porous plate 121 is provided to an upper portion of the lower body 120. The porous plate 121 forms a lower surface of a space for accommodating the mixed solution, when the lower body 120 is coupled to the upper body 120. That is, the mixed solution is accommodated in the space defined by the upper body 110 and the porous plate 121 of the lower body 120. Further, the mixed solution accommodated in the mixed solution container 100 is suctioned by a suction unit 310 described below, such that the mixed solution flows into the suction unit 310 through the porous plate 121. Further, the buffer portion 122 and the filter 123 may be disposed above the porous plate 121.

The buffer portion 122 may be disposed between the porous plate 121 and the filter 123. The buffer portion 122 serves to compress and buffer the filter 123 with respect to a slide 10 in the course of stamping cells filtered by the filter 123 to the slide 10. The buffer portion 122 may be formed of an elastic material for buffering.

The filter 123 serves to filter cells from the mixed solution passing therethrough. That is, the filter 123 serves to filter cells. The filter 123 may be, for example, a filter. However, it should be understood that the present invention is not limited thereto and that the filter 123 may have any configuration so long as the filter can filter cells from the mixed solution. Further, the cells filtered by slide 10 are stamped to the slide 10 described below.

The porous plate 121, the buffer portion 122, and the slide 10 may have a rectangular shape when viewed in top plan view. In this embodiment, when the cells filtered by slide 10 are smeared onto the slide 10, a sample of the cells remaining on the slide 10 may have a rectangular shape. Such a rectangular sample can further reduce time consumption for microscopic examination with respect to an overall area of the sample as compared with a circular sample, thereby providing examination efficiency.

The outlet 124 is a passage through which the filtered solution obtained by filtering the cells from the mixed solution is discharged from the mixed solution container 100. In one exemplary embodiment, as shown in FIG. 5 and FIG. 6, the outlet 124 may be disposed at the lowermost portion of the mixed solution container 100, without being limited thereto. In addition, the outlet 124 may have a hollow cylindrical shape, without being limited thereto.

By way of example, the outlet 124 may be coupled to the suction unit 310 by being inserted into the hollow space of the suction unit. Further, a sealing member (not shown) may be disposed between the outlet 124 and the suction unit 310 to secure air-tightness therebetween. As such, when air-tightness between the mixed solution container 100 and the suction unit 310 of the tray 300 is maintained by the sealing member, suction force supplied through the suction unit 310 can be directly transferred to the mixed solution container 100. Furthermore, in addition to the sealing member for securing air-tightness between the outlet 124 and the suction unit 310, a sealing member 130 may be disposed between the upper body 110 and the lower body 120 to secure air-tightness therebetween. This will be described below.

The sealing member 130 is disposed so as to maintain air-tightness therebetween when the upper body 110 is coupled to the lower body 120. In one exemplary embodiment, the sealing member 130 may be disposed between the inner protrusion 112 of the upper body 110 and the lower body 120, without being limited thereto. The sealing member 130 may be realized by, for example, an elastic material such as a rubber or silicone material, without being limited thereto.

The case 200 constitutes an outer appearance of the cell smearing apparatus. For example, the case 200 may be configured such that members described hereinafter can be accommodated in the case 200 or may be disposed thereon. The case 200 may have, for example, a parallelepiped shape, as shown in FIG. 1, without being limited thereto.

For example, the mixed solution container accommodation unit 210, a slide accommodation portion 220, partitions 230, a display 240, a button 250, a power supply 260, a preservation solution supplier (not shown) and a waste solution outlet (not shown) may be disposed on the case 200.

The mixed solution container accommodation unit 210 may be disposed, for example, on an upper surface 201 of the case 200 and serve to accommodate the mixed solution container 100. The mixed solution container accommodation unit 210 may include, for example, a groove 211, into which the outer protrusion 111 of the mixed solution container 100 having a shape corresponding to the groove 211 can be inserted.

The slide accommodation portion 220 is disposed, for example, on the upper surface 201 of the case 200 and serves to accommodate the slide 10. The slide accommodation portion 220 may include, for example, a groove 221, into which the slide 10 having a shape corresponding to the groove 221 may be inserted and supported thereby.

The slide accommodation portion 220 may be provided to a lower portion of the mixed solution container accommodation unit 210. This structure does not require removal of the upper body 110 during a process of stamping the lower body 120 to the slide 10, with the mixed solution container 100 separated. In an alternative embodiment, the slide accommodation portion 220 may be integrally formed with the mixed solution container accommodation unit 210. In this embodiment, it is necessary to insert the slide 10 after removal of the upper body 110 for stamping of cells.

The partitions 230 may be provided to divide an internal space of the case 200. A motor 430, the pump 600, and other components may be mounted on the partitions 230.

The display 240 provides a screen for displaying a current operation state of the cell smearing apparatus, and the like. By way of example, the display 240 can show a sensed value obtained through the sensor unit 700 described below, and may output an alert message, as needed. The display 240 may display an output value in response to compression on a button 250 described below. By way of example, the display 240 may be disposed on a front side 202 of the case 200, without being limited thereto. By way of example, the display 240 may be realized by a liquid crystal display (LCD), without being limited thereto. Alternatively, the display 240 may be realized by a touch panel, which advantageously provides a function of the button 250.

A command for controlling the cell smearing apparatus may be input through the button 250. By way of example, the button 250 may be disposed on the front side of the case 202, as shown in FIG. 1. Further, the button 250 may be disposed near the display 240. This structure provides user convenience by allowing a user operating the button 250 to confirm through the display 240 whether the button 250 is normally operated. By way of example, the button 250 may be composed of four buttons, that is, a power button, an input button, an up button and a down button, without being limited thereto.

The power supply 260 may be provided, for example, to a backside 203 of the case 200 to receive power from an external power source and supply the power to the cell smearing apparatus as needed. Although a relationship between the power supply 260 and other components is not shown in FIG. 2 and FIG. 3, the power supply 260 may be connected to other components requiring supply of power via electric lines to supply power to the other components.

The preservation solution supplier (not shown) serves to additionally supply a preservation solution to the mixed solution container 100 when it is determined through a concentration analyzer (not shown) described below that the mixed solution accommodated in the mixed solution container 100 has an excessively high concentration. The preservation solution supplier may be disposed inside or outside the case 200 and may supply the preservation solution to the mixed solution container 100 through a tube (not shown).

A waste solution outlet (not shown) provides a passage through which the filtered solution and the drain respectively discharged through a filtered solution discharge portion 330 and a drain discharge portion 340 are discharged outside. The waste solution outlet may be provided, for example, to a side surface 204 of the case 200, without being limited thereto.

By way of example, the tray 300 may include the suction unit 310, a drain inlet 320, the drain accommodation unit (not shown), the filtered solution discharge portion 330, the drain discharge portion 340, a screw groove 350, and guide grooves 360.

The suction unit 310 may be separably coupled to the outlet 124 of the mixed solution container 100. The suction unit 310 may include, for example, a hollow space 311 and may have a shape corresponding to the shape of the outlet 124 of the mixed solution container 100. With this structure, the suction unit 310 may be coupled to the outlet 124 by being inserted into the hollow space 311 of the suction unit 310. The suction unit 310 coupled to the outlet 124 supplies suction force to the mixed solution accommodated in the mixed solution container 100. Such a suction force may be generated by the pump 600 described below. As described above, the sealing member may be disposed between the suction unit 310 and the outlet 124 to secure air-tightness therebetween.

The drain inlet 320 may be disposed to surround an outer surface of the suction unit 310. This structure allows the drain not flowed into the suction unit 310 to be accommodated in the drain accommodation unit disposed within the tray 300 instead of flowing to the outside of the tray 300. That is, the filtered solution suctioned by the suction force of the pump 600 flows into the tray 300 through the suction unit 310, and the drain discharged by separation of the upper body 110 from the lower body 120 flows into the tray through the drain inlet 320. On the other hand, the filtered solution suctioned through the suction unit 310 may be discharged through the filtered solution discharge portion 330, and the drain accommodated in the drain accommodation unit may be discharged through the drain discharge portion 340.

The drain accommodation unit (not shown) is formed, for example, inside the tray 300 to accommodate the drain.

The filtered solution discharge portion 330 is disposed at one side of the tray 300 and communicates with the suction unit 310 to allow the filtered solution having flowed into the filtered solution discharge portion 330 through suction unit 310 to flow into the valve 500 through a first tube 810.

The drain discharge portion 340 is disposed at one side of the tray 300 and communicates with the drain accommodation unit to allow the drain accommodated in the drain accommodation unit to flow into the valve 500 through a second tube 820.

The screw groove 350 may have threads formed on an inner circumferential surface thereof. The screw groove 350 may be screwed to a transfer screw 410 disposed inside the case 200. That is, the screw groove 350 may include threads corresponding to the transfer screw 410. With this structure, when the transfer screw 410 is rotated, the tray 300 formed with the screw groove 350 can be transferred up or down.

Guide rods 420 may be disposed inside the case 200 and pass through the guide grooves 360. The guide grooves 360 may have a shape corresponding to, for example, the shape of the guide rods 420. With this structure, when the tray 300 is transferred up or down, the tray 300 can be transferred vertically without shaking or deviating. Although two guide grooves 360 and two guide rods 420 are shown by way of example in FIG. 2, it should be understood that the present invention is not limited thereto.

The transfer member 400 serves to transfer the tray 300. By way of example, the transfer member 400 may include a transfer screw 410, guide rods 420, a motor 430, pulleys 440, and a belt 450.

The transfer screw 410 may have threads formed on an outer circumferential surface thereof and may be disposed inside the case 200 to be perpendicular to a bottom surface 205 of the case 200. The transfer screw 410 may be screwed to the screw groove 350 of the tray 300.

The guide rods 420 may be disposed inside the case 200 to be perpendicular to the bottom surface of the case 200. The guide rods 420 may pass through the guide grooves 360 of the tray 300, respectively.

The motor 430 may supply rotational force to the transfer screw 410. The motor 430 receives power from the power supply 260 to rotate the transfer screw 410. By way of example, the motor 430 may rotate the transfer screw 410 in the clockwise direction and in the counterclockwise direction. With this structure, the motor 430 can transfer the tray 300 screwed to the transfer screw 410 in an upward or downward direction.

In one exemplary embodiment, the motor 430 may be a stepper motor or an encoder motor. In this embodiment, since the revolutions per minute of the motor 430 can be controlled or can be calculated, it is possible to move the tray 300 to an accurate target location.

By way of example, the motor 430 may be directly connected to the transfer screw 410 or may be connected thereto via the pulleys 440 and the belt 450, as shown in FIG. 2 and FIG. 3. More specifically, the pulleys 440 are provided to the motor 430 and the transfer screw 410, respectively, and the belt 450 connects the pulley 440 of the motor 430 to the pulley 440 of the transfer screw 410 such that rotational force of the motor 430 can be transferred to the transfer screw 410.

The valve 500 serves to selectively control discharge of the filtered solution and the drain.

The valve 500 may be, for example, a 3-way valve, without being limited thereto. In one exemplary embodiment, the valve 500 may include a first inlet 510, a second inlet 520, an outlet 530, and a shut-off unit (not shown).

The first inlet 510 may be connected to the filtered solution discharge portion 330 through the first tube 810. That is, the filtered solution may flow through the first inlet 510.

The second inlet 520 may be connected to the drain discharge portion 340 through the second tube 820. That is, the drain may flow through the second inlet 520.

The outlet 530 acts as a passage through which a waste solution having flowed through the first inlet 510 and the second inlet 520 is discharged.

The shut-off unit selectively opens or closes the first inlet 510 and the second inlet 520. That is, the shut-off unit may shut connection between the first inlet 510 and the outlet 530 or connection between the second inlet 520 and the outlet 530. Although the shut-off unit has been described above as a single component, a separate shut-off member may be provided to each of the first inlet 510 and the second inlet 520 so as to act as the shut-off unit.

The pump 600 provides suction force to the suction unit 310 of the tray 300. That is, the mixed solution accommodated in the mixed solution container 100 is suctioned by the pump 600. By way of example, the pump 600 may be a peristaltic tube pump which is connected to the motor 610 and suctions fluid by squeezing a tube. With this structure, it is possible to achieve accurate control of a suction amount of the mixed solution.

By way of example, the pump 600 may be connected to the outlet 530 through a third tube 830. The third tube 830 may be connected to a waste solution outlet (not shown) through the pump 600.

The sensor unit 700 serves to sense variation of the mixed solution suctioned by the suction unit 310. A controller 1000 described below uses the value sensed by the sensor unit 700 when controlling a speed of suctioning the mixed solution by the suction unit 310.

The sensor unit 700 may be, for example, a pressure sensor configured to sense a suction pressure with respect to the mixed solution. The sensor unit 700 may be connected to, for example, a wire type connector 840 through a fourth tube 850. The wire type connector 840 is disposed on the first tube 810 to be connected to the fourth tube 850. The pressure sensor can sense the suction pressure of the mixed solution generated in the first tube 810 through the fourth tube 850.

By way of example, the sensor unit 700 may be provided to the partitions 230, without being limited thereto.

The tubes 810, 820, 830, 850 and the wire type connector 840 are omitted in FIG. 2 and FIG. 3. As shown in FIG. 4, the first tube 810 may connect the filtered solution discharge portion 330 and first inlet 510. The second tube 820 may connect the drain discharge portion 340 to the second inlet 520. The third tube 830 may connect the outlet 530 to the pump 600. In addition, the third tube 830 may be connected to the waste solution outlet through the pump 600. The wire type connector 840 is disposed on the first tube 810 and may be connected to the fourth tube 850 described below. The fourth tube 850 may connect the wire type connector 840 to the sensor unit 700.

The concentration analyzer (not shown) may be disposed near the mixed solution container accommodation unit 210 of the case 20U to sense the concentration of the mixed solution in the mixed solution container 100 accommodated in the mixed solution container accommodation unit 210. When it is determined through the concentration analyzer that the mixed solution has a high concentration, the preservation solution may be additionally supplied to the mixed solution container through the preservation solution supplier. With the structure in which the concentration of the mixed solution suctioned by the suction unit 310 is controlled in this way, the cell smearing apparatus has an advantage in that cells filtered by the filter 123 are uniformly distributed.

In one exemplary embodiment, the concentration analyzer may include a light emitting portion (not shown) and a light receiving portion (not shown). In the concentration analyzer, the light emitting portion emits light to the mixed solution container accommodation unit 210 and the light receiving portion receives the light having passed through the mixed solution container accommodation unit 210, whereby the concentration of the mixed solution accommodated in the mixed solution container accommodation unit 210 can be sensed by the concentration analyzer.

The controller 900 serves to control the speed of suctioning the mixed solution by the suction unit 310 based on the value sensed by the sensor unit 700. For example, when a value sensed by the sensor unit 700 reaches a predetermined value, the controller 900 may control the suction unit 310 to reduce the speed of suctioning the mixed solution.

Next, a cell smearing method according to one exemplary embodiment of the present invention will be described with reference to the accompanying drawings.

Figure 7:
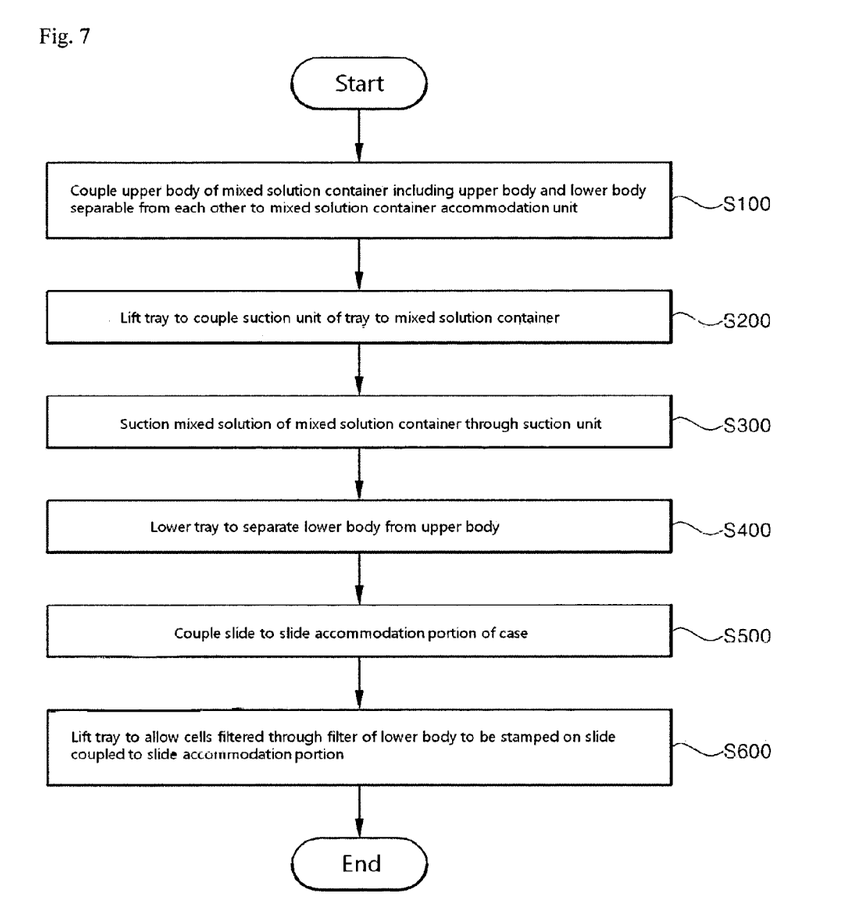
FIG. 7 is a flowchart of a cell smearing method according to one exemplary embodiment of the present invention.
Figure 8:
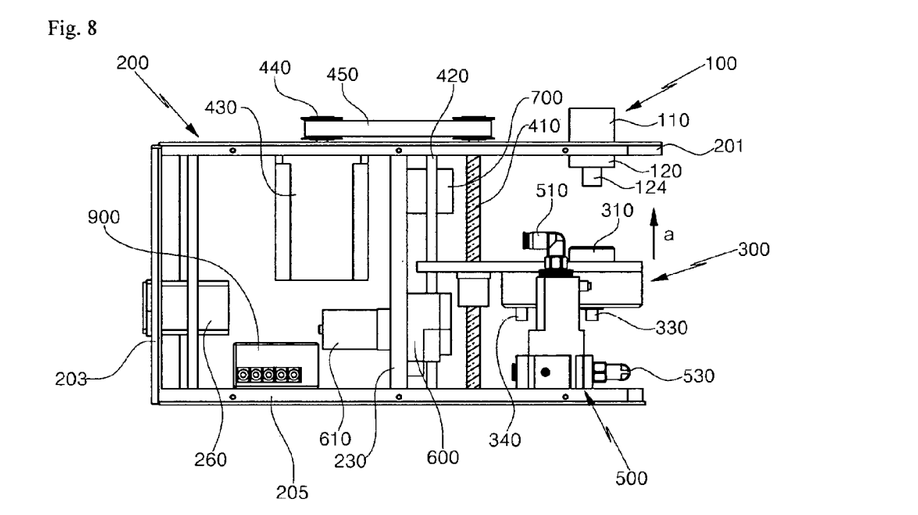
FIGS. 8 to 11 are time-series sectional views illustrating the cell smearing method according to the exemplary embodiment of the present invention.

FIG. 7 is a flowchart of a cell smearing method according to one exemplary embodiment of the present invention, and FIGS. 8 to 11 are time-series sectional views illustrating the cell smearing method according to the exemplary embodiment of the present invention.

In the cell smearing method according to one exemplary embodiment, first, the upper body 110 of the mixed solution container 100 including the upper body 110 and the lower body 120 separable from each other is coupled to the mixed solution container accommodation unit 210 of the case 200 (S100). More specifically, the upper body 110 may be coupled to the mixed solution container accommodation unit 210 by inserting the outer protrusion 111 of the upper body 110 into the groove 211 of the mixed solution container accommodation unit 210.

Figure 9:
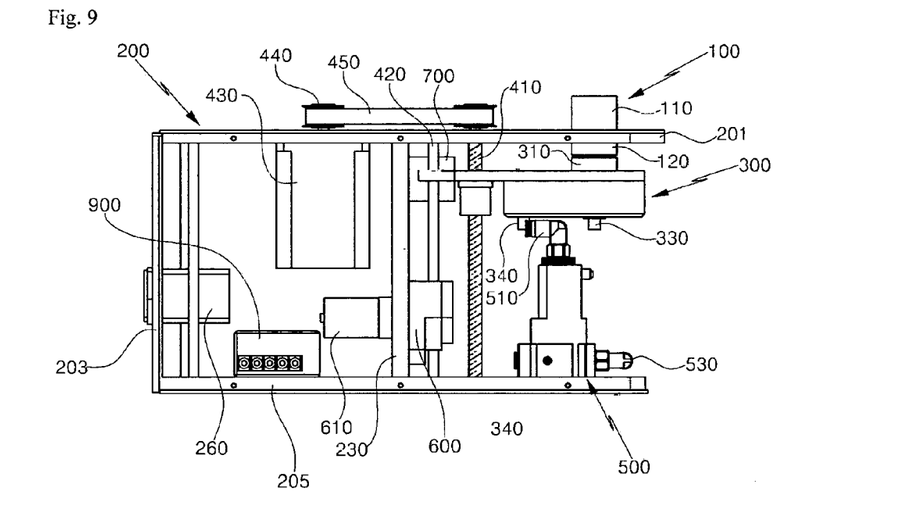

Thereafter, the tray 300 is lifted (as indicated by arrow a of FIG. 8) such that the suction unit 310 of the tray 300 is coupled to the mixed solution container 100 (S200) (see FIG. 9). More specifically, the mixed solution container 100 may be coupled to the tray 300 in such a way that the outlet 124 of the mixed solution container 100 is inserted into the hollow space 311 of the suction unit 310. Here, the sealing member (not shown) is disposed between the mixed solution container 100 and the suction unit 310 to maintain airtightness therebetween.

Further, the tray 300 may be lifted by the transfer member 400 provided as a component for transferring the tray 300 upwards or downwards. The transfer member 400 includes, for example, the motor 430 and the transfer screw 410 rotated by the motor 430 and may transfer the tray 300 screwed to the transfer screw 410 upwards or downwards.

Thereafter, a mixed solution in the mixed solution container 100 is suctioned through suction unit 310 (S300). More specifically, the suction unit 310 communicates with the pump 600 and can suction the mixed solution from mixed solution container 100 using suction force of the pump 600. Then, the mixed solution placed in the upper body 110 of the mixed solution container 100 flows into the suction unit 310 through the filter 123 of the lower body 120. In this way, cells are filtered from the mixed solution by the filter 123 and only a filtered solution from which the cells are removed is introduced into the suction unit 310.

Here, as the amount of the cells filtered by the filter 123 increases, a flow passage formed in the filter 123 is narrowed. Thus, a negative pressure (pressure for suctioning the mixed solution) generated in the suction unit through the pressure sensor corresponding to one example of the sensor unit 700 is gradually increased after a predetermined period of time. In one exemplary embodiment, when the pressure detected by the pressure sensor reaches a predetermined pressure, the suction unit 310 is controlled to reduce the speed of suctioning the mixed solution. As a result, advantageously, the cells are uniformly distributed on the filter 123 and are prevented from agglomerating or being accumulated in several layers on the filter 123. In other words, according to this exemplary embodiment, it is possible to solve a problem that, when the suction unit 310 is not controlled to reduce the speed of suctioning the mixed solution, the mixed solution can be discharged through a flow passage of the filter 123 in which the cells have already been received, thereby causing accumulation and agglomeration of the cells.

Alternatively, when the pressure detected by the pressure sensor reaches a predetermined pressure, the suction unit 310 may be controlled to stop suctioning of the mixed solution. However, when operation of the suction unit 310 is abruptly stopped, there is a problem in that a large amount of drains are not suctioned by the suction unit 310 and can flow at a high speed to the outside to sweep the cells filtered by and remaining on the filter 123 such that some of the cells can be exposed together with the drains, as compared with controlling the suction unit 310 to reduce the suction speed.

In addition, according to the exemplary embodiment, even when the pressure detected by the pressure sensor does not reach a predetermined pressure, the suction unit 310 may be controlled to reduce the speed of suctioning the mixed solution over time.

Figure 10:
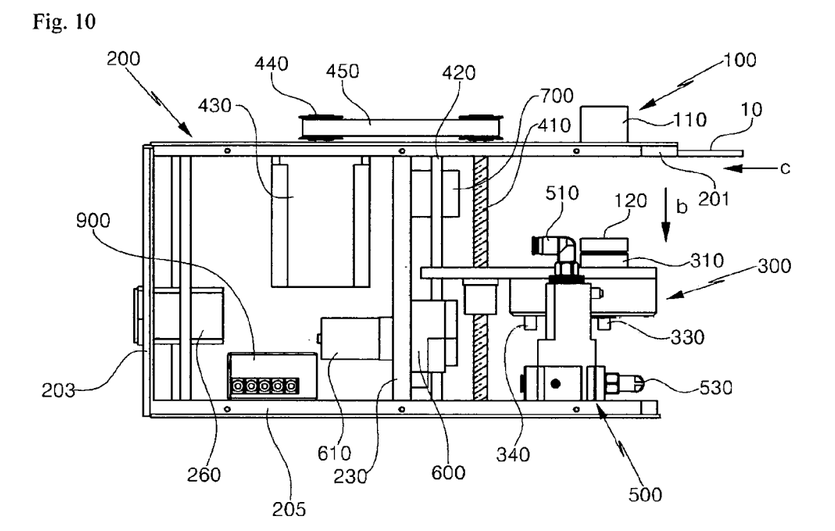

Then, the tray 300 is lowered to separate the upper body 110 from the lower body 120 (S400) (as indicated by arrow b in FIG. 10). Here, the tray 300 may be lowered by the transfer member 400 as in the case of lifting the tray. More specifically, the tray 300 may be lowered by the transfer member 400 and the lower body 120 coupled to the tray 300 may also be lowered. Here, the upper body 110 coupled to the mixed solution container accommodation unit 210 of the case 200 is separated from the lower body 120 and is maintained in a state of being coupled to the mixed solution container accommodation unit 210 of the case 200. Then, the mixed solution remaining in the upper body 110 instead of being suctioned through the filter 123 flows along the outer periphery of the lower body 120 due to separation of the upper body 110 from the lower body 120. In one exemplary embodiment, the mixed solution (that is, the drain) flowing along the outer periphery of the lower body 120 is introduced through the drain inlet 320 formed to surround the outer circumference of the suction unit 310 of the tray 300. The drain introduced through the drain inlet 320 can be accommodated in the drain accommodation unit.

Then, a slide 10 is coupled to the slide accommodation portion 220 of the case 200 (S500) (as indicated by arrow c in FIG. 10). More specifically, the slide 10 is inserted into and secured to the groove 211 of the slide accommodation portion 220 having a shape corresponding to the shape of the slide 10.

Figure 11:
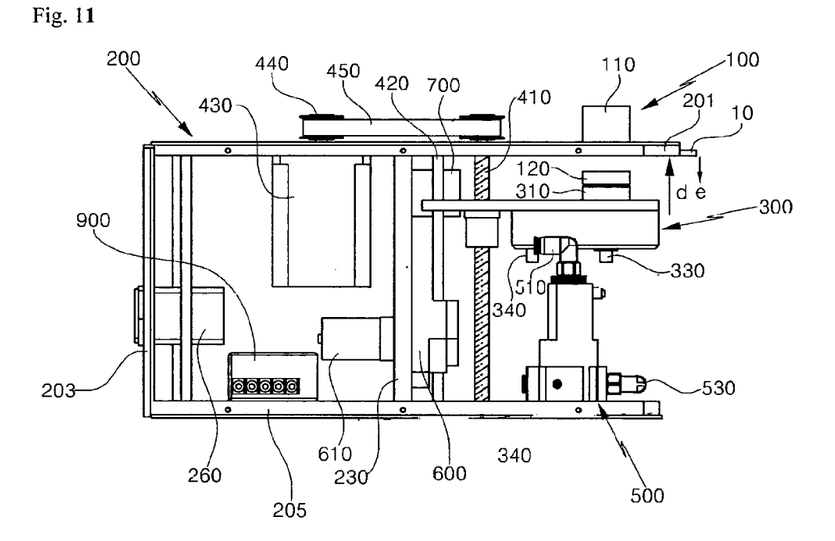

Thereafter, the tray 300 is lifted to allow the cells filtered by the filter 123 of the lower body 120 to be stamped on the slide 10 coupled to the slide accommodation portion 220 (S500) (as indicated by arrows d and e in FIG. 11). More specifically, stamping may be carried out in such a way that the tray 300 is lifted to allow the filter 123 to be brought into contact with the slide 10 and to be separated therefrom. Through this operation, a sample of the cells can be smeared onto the slide 10.

Additionally, in the cell smearing method according to this exemplary embodiment, before Step S300, the concentration analyzer measures the concentration of the mixed solution in the mixed solution container 100 accommodated in the mixed solution container accommodation unit 110, and, when the concentration of the mixed solution measured by the concentration analyzer is higher than a predetermined value, the preservation solution supplier may additionally supply a preservation solution to the mixed solution container 100. As a result, there is an advantage in that a desired concentration of the mixed solution can be maintained, thereby minimizing agglomeration or accumulation of the cells filtered by the filter 123.

Next, the cell smearing method according to the exemplary embodiment will be further described with reference to a flow of the mixed solution.

Initially, the mixed solution is accommodated in the mixed solution container 100.

Then, the mixed solution is suctioned by the suction unit 310 and introduced into the valve 500 through the filtered solution discharge portion 330, the first tube 810 and the first inlet 510 of the tray 300. Herein, the mixed solution having passed through the filter 123 of the mixed solution container 100 in this way is referred to as the filtered solution.

Further, upon separation of the upper body 110 from the lower body 120, the mixed solution exposed to the outside instead of passing through the filter 123 flows into the drain accommodation unit through the drain inlet 320 of the tray 300 and is then accommodated therein. Then, the mixed solution is introduced into the valve 500 through the drain discharge portion 340, the second tube 820 and the second inlet 520. Herein, the mixed solution having flowed in this way and not having passed through the filter 123 of the mixed solution container 100 is referred to as the drain.

In the valve 500, the shut-off unit selectively opens or closes the first inlet 510 and the second inlet 520 to determine whether the filtered solution or the drain will be provided through the valve 500.

Both the filtered solution and the drain introduced into the valve 500 are discharged through the waste solution outlet via the outlet 530 and the pump 600. Herein, both the filtered solution and the drain introduced into the valve 500 and discharged through the waste solution outlet are commonly referred to as waste solution.

On the other hand, in the cell smearing apparatus according to the one exemplary embodiment described above, since the mixed solution container accommodation unit 210 separably accommodating the mixed solution container 100 and the slide accommodation portion 220 in which cell stamping is performed are disposed on the upper surface of the case 200 and exposed outside, there can be a problem of contamination due to direct exposure of the mixed solution container accommodation unit 210 and the slide accommodation portion 220 to the outside. In addition, due to openings of the mixed solution container accommodation unit 210 and the slide accommodation portion 220, foreign contaminants can be easily introduced into the tray 300 and other components of the apparatus.

Figure 12:
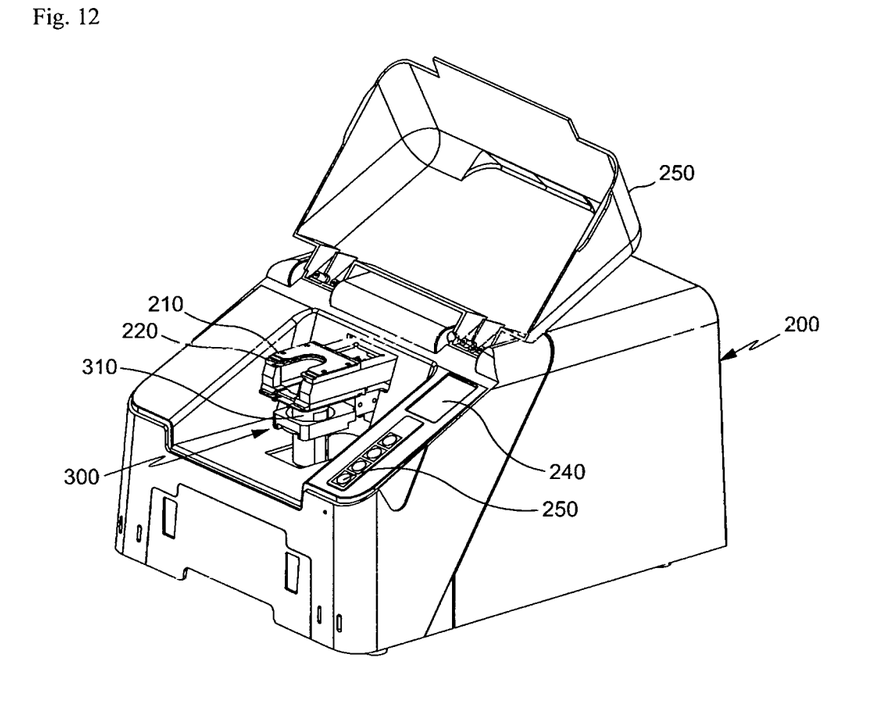
FIG. 12 is a perspective view of a cell smearing apparatus according to another exemplary embodiment of the present invention.

A structure capable of preventing contamination of inner components by external contaminants is shown in FIG. 12.

FIG. 12 is a perspective view of a cell smearing apparatus according to another exemplary embodiment of the present invention.

Referring to FIG. 12, the mixed solution container accommodation unit 210 separably accommodating the mixed solution container 100, the slide accommodation portion 220 in which cell stamping is performed, and the tray 300 coupled to the mixed solution container 100 to discharge a mixed solution, a filtered solution, and the like are disposed within the case 200, and a cover 250 is provided to the case to protect such internal smearing components from an external environment. The cover 250 can be rotated about a hinge and can be conveniently opened or closed by user manipulation. Accordingly, in a standby state in which cell smearing is not performed, the cover 250 is closed to block the internal smearing components from an external environment to prevent contamination by external contaminants and during cell smearing, the cover 250 is opened to allow cell smearing to be carried out with the internal smearing components exposed to the outside.

Here, although the display 240 and the button 250 can also be opened or closed by the cover 250 as shown in FIG. 12, the display 240 and the button 250 may be formed on an outer surface of the case, as shown in FIG. 1.

Although all components are illustrated as being coupled to each other into one piece or being operated as one-piece in the above exemplary embodiments, it should be understood that the present invention is not limited thereto. That is, these components may be selectively coupled to each other as plural structures as well, unless context clearly indicates otherwise. It will be further understood that the terms "includes", "comprises" and/or "have (has)" when used in this specification, specify the presence of stated features, steps, operations, elements, and/or components, but do not preclude the presence or addition of one or more other features, steps, operations, elements, components, and/or groups. Unless otherwise defined herein, all terms including technical or scientific terms used herein have the same meanings as commonly understood by those skilled in the art to which the present invention pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein Although some exemplary embodiments have been described herein, it should be understood by those skilled in the art that these embodiments are given by way of illustration only, and that various modifications, variations and alterations can be made without departing from the spirit and scope of the invention. Therefore, the embodiments and the accompanying drawings should not be construed as limiting the technical spirit of the present invention, but should be construed as illustrating the technical spirit of the present invention. The scope of the invention should be interpreted according to the following appended claims as covering all modifications or variations derived from the appended claims and equivalents thereof.

The invention claimed is:

1. A cell smearing apparatus comprising:
    a mixed solution container accommodation unit accommodating a mixed solution container containing a mixed solution of cells and a preservation solution, the mixed solution container comprising an upper body accommodating the mixed solution, a lower body provided with a filter unit filtering the cells in the mixed solution and detachably coupled to the upper body, and a sealing member for securing air-tightness between the upper body and the lower body coupled to each other;
    a suction unit suctioning the mixed solution from the mixed solution container accommodated in the mixed solution container accommodation unit, the suction unit provided to a tray;
    a transfer member transferring the tray in an up-down direction and controlling a transferred distance of the tray through a stepper motor or an encoder motor;
    a sensor unit sensing variation of the mixed solution suctioned by the suction unit; and
    a controller controlling a suctioning speed of the suction unit based on a value sensed by the sensor unit;
    wherein the filter unit comprises a filter having a film shape and filtering the cells in the mixed solution, and comprises a buffer portion provided to one side of the filter and compressing and buffering the filter with respect to a slide when the filtered cells are stamped on the slide, the filter and the buffer portion having a rectangular shape;
    wherein the tray comprises a drain accommodation unit accommodating a drain discharged outside instead of passing through the filter when the upper body is separated from the lower body, and the tray is connected to a valve, the valve comprising:
        a first inlet communicating with the suction unit;
        a second inlet communicating with the drain accommodation unit;
        an outlet through which a fluid having flowed through the first inlet and the second inlet is discharged; and
        a shut-off unit selectively opening or closing the first inlet and the second inlet.

2. The cell smearing apparatus according to claim 1, wherein the sensor unit is a pressure sensor for sensing a pressure of suctioning the mixed solution, and the controller controls the suction unit to suction the mixed solution at a reduced speed when a pressure of suctioning the mixed solution sensed by the pressure sensor reaches a predetermined pressure.

3. The cell smearing apparatus according to claim 1, further comprising:

a concentration analyzer measuring a concentration of the mixed solution in the mixed solution container accommodated in the mixed solution container accommodation unit; and a preservation solution supplier additionally supplying the preservation solution to the mixed solution container accommodation unit when the concentration of the mixed solution measured by the concentration analyzer exceeds a predetermined value.

4. The cell smearing apparatus according to claim 1, wherein the suction unit is connected to a pump for suctioning the mixed solution, the pump being a peristaltic tube pump.

* * * * *